United States Patent [19]

Tretinyak et al.

[11] 4,386,606
[45] Jun. 7, 1983

[54] SYRINGE LOCK

[75] Inventors: Carl W. Tretinyak; Thomas A. Burton, both of Rochester, Minn.

[73] Assignee: Waters Instruments, Inc., Rochester, Minn.

[21] Appl. No.: 210,290

[22] Filed: Nov. 28, 1980

Related U.S. Application Data

[63] Continuation-in-part of Ser. No. 106,525, Dec. 26, 1979, abandoned.

[51] Int. Cl.³ .............................................. A61M 5/00
[52] U.S. Cl. .................................................. 604/220
[58] Field of Search ........ 128/218 R, 218 PA, 218 C, 128/213, 215, 216, 234; 222/326, 386

[56] References Cited

U.S. PATENT DOCUMENTS

| 1,526,056 | 2/1925 | Eisele | 128/218 PA |
|---|---|---|---|
| 2,216,354 | 10/1940 | Pletcher | 128/234 |
| 2,869,541 | 1/1959 | Helmer et al. | 128/218 |
| 3,797,487 | 3/1974 | Schmidt | 128/218 PA |
| 3,831,602 | 8/1974 | Broadwin | 128/218 PA |
| 3,882,849 | 5/1975 | Jamshidi | 128/218 C X |
| 3,938,505 | 2/1976 | Jamshidi | 128/218 C X |
| 4,011,868 | 3/1977 | Friend | 128/234 |
| 4,024,865 | 5/1977 | Howlett | 128/218 PA |
| 4,173,225 | 11/1979 | Newman | 128/234 |

FOREIGN PATENT DOCUMENTS

| 203683 | 11/1907 | Fed. Rep. of Germany . |
|---|---|---|
| 381773 | 2/1923 | Fed. Rep. of Germany . 128/218 PA |
| 1065573 | 9/1959 | Fed. Rep. of Germany . |
| 4207 | of 1910 | United Kingdom . |
| 856659 | 12/1960 | United Kingdom . |

Primary Examiner—John D. Yasko
Attorney, Agent, or Firm—James R. Haller

[57] ABSTRACT

A syringe having a barrel and a plunger moveable axially in the barrel is provided with locking means for locking the plunger to the barrel. The locking means includes cam means carried between the barrel and the plunger, and means for moving the cam into a position forcing the plunger into binding contact with the barrel.

17 Claims, 14 Drawing Figures

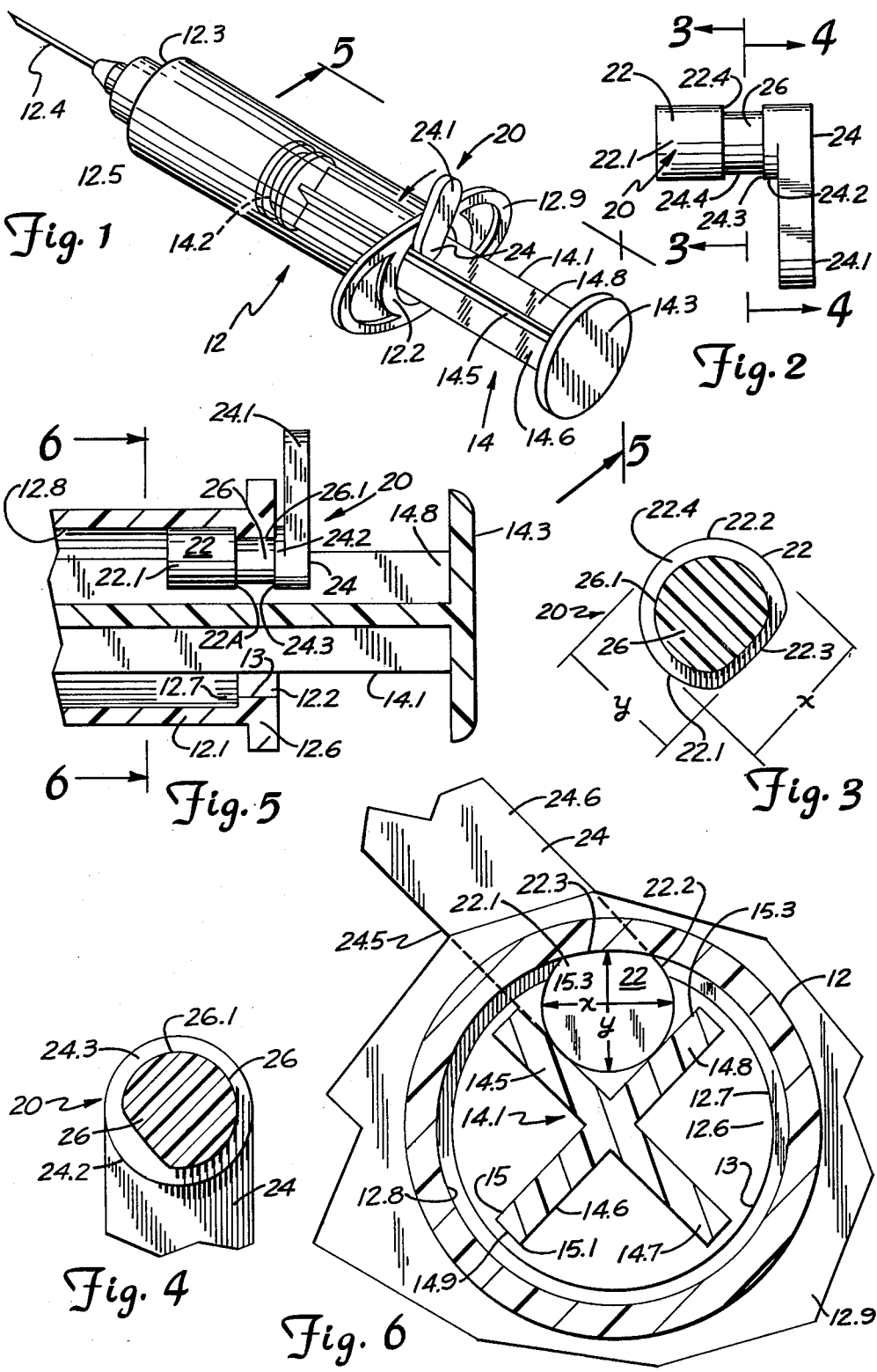

SYRINGE LOCK

This application is a continuation-in-part of application Ser. No. 106,525, filed Dec. 26, 1979, now abandoned.

TECHNICAL FIELD

The present invention relates to syringes such as hypodermic syringes employed in the field of medicine, and particularly relates to locking devices for such syringes.

BACKGROUND ART

Syringes have a variety of medical and non-medical applications. In the field of medicine, syringes may be employed to withdraw blood, inject medicines, and, in association with other devices, to aid in biopsy procedures and bone-marrow transplant procedures. In the industrial field, syringes (commonly modified or unmodified medical syringes) may be employed, for example, to withdraw samples of fluids or gases from reactors, and to dispense adhesives or other fluid compositions. A medical syringe generally includes a barrel, commonly of plastic, and a plunger that is slideable within the barrel and which includes a piston that sealingly fits within the barrel. The plunger commonly is provided with an accessible finger grip at its proximal end for pushing and pulling the plunger into and out of the barrel, and the barrel itself may have opposing finger grips at its proximal end. Medical syringes have been made in a variety of sizes and configurations, and are well-known in the medical and industrial fields.

Syringe barrels often contain volume markings, and in a widely used commercial syringe, the barrel is made of a translucent plastic material so that the position of the piston at the end of the plunger can be viewed through the barrel walls. The volumetric markings carried by the barrel are then aligned with the distal end of the piston to provide volumetric readings.

It is often desirable to lock the plunger of a syringe at a given position within the barrel. For example, the soft-tissue biopsy procedure outlined in U.S. Pat. No. 3,882,849 requires the piston to be retracted to a certain point within the barrel to provide a partial vacuum within the barrel, and the piston should then be positively prevented from returning, under the influence of the pressure differential across it, toward its initial position. As another example, it may be desired to withdraw a particular amount of fluid from an organ, such as commonly is done in amniocentesis procedures, the fluid being retained in the syringe until it can be discharged into an appropriate receptacle. While the fluid is in the syringe, care should be taken that the plunger is not accidentally moved. It may be desirable to draw into each of a pair of syringes a particular volume of a reactive chemical; for example, one syringe may contain a reactive epoxide resin and another syringe may contain a particular volume of an amine "hardener" reactive with the resin. Since the relative volumes of the resin and hardener that are dispensed may be critical to the properties of the resulting resin, it is desirable that the plungers be prevented from moving within the barrels of the syringes until the resin and hardener are to be dispensed from the syringes.

U.S. Pat. No. 3,882,849 discloses a biopsy needle having a toothed plunger, the teeth of which can be engaged with a plate at the proximal end of the barrel at given positions of the plunger within the barrel. A somewhat similar syringe is shown in U.S. Pat. No. 3,938,505. Syringes of this type require significant additional manufacturing steps and expense, and the sharp edges of the teeth, such as those shown in U.S. Pat. No. 3,882,849, can catch, for example, on surgical gloves worn by doctors or nurses.

DISCLOSURE OF INVENTION

The present invention provides locking means for a syringe, the syringe having a barrel and a plunger moveable axially in the barrel. The locking means includes cam means carried by the barrel between the barrel and plunger, and means for moving the cam means into a position forcing the plunger in a direction generally normal to its axis into binding contact with the barrel. The cam means desirably is positioned adjacent the proximal open end of the barrel, and the means for moving the cam preferably includes a small handle attached at one end to the cam and extending generally normally outwardly from the axis of the barrel at its open end. The cam means desirably includes retaining means coacting with the barrel for retaining the cam in an axially fixed position with respect to the barrel.

BRIEF DESCRIPTION OF DRAWING

FIG. 1 is a perspective view of a syringe including a locking means of the invention;

FIG. 2 is a plan view of the locking means shown in FIG. 1;

FIG. 3 is a cross-sectional view taken across line 3—3 of FIG. 2;

FIG. 4 is a cross-sectional view taken along line 4—4 of FIG. 2;

FIG. 5 is a broken-away, cross-sectional view taken along line 5—5 of FIG. 1;

FIG. 6 is a broken-away, cross-sectional view taken along line 6—6 of FIG. 5;

BEST MODE FOR CARRYING OUT THE INVENTION

Figure 7:
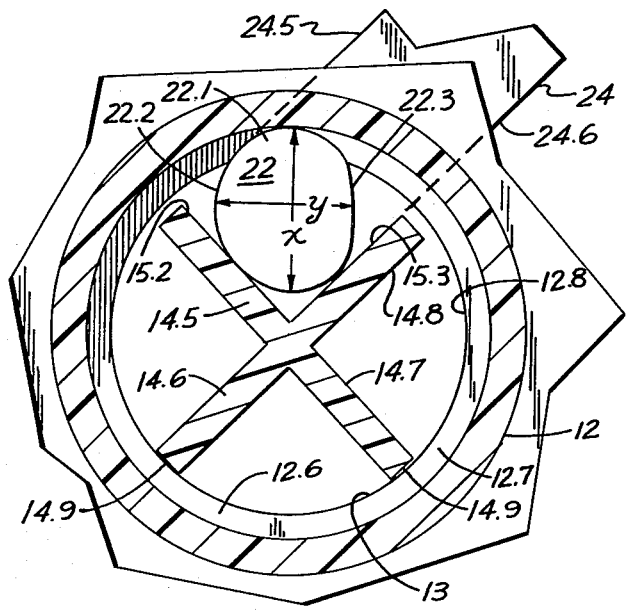
FIG. 7 is a cross-sectional view similar to that of FIG. 6 but showing the locking means in a different position.

A typical standard medical syringe is designated generally as 12 in FIG. 1. The syringe includes a barrel (12.1) with an open proximal end (12.2) and a constricted distal end (12.3). For purposes of example, a hypodermic needle (12.4) is shown connected to the distal end of the syringe by means of a common fitting such as a luer lock fitting (12.5). At its proximal end, the barrel is provided with an inwardly directed lip (12.6) which in turn provides a distally-facing, annular shoulder (12.7). The smooth interior surface (12.8) of the barrel extends substantially throughout the length of the barrel, and the barrel desirably is of uniform diameter. Finger grips (12.9) (FIG. 1) extend outwardly from the open proximal end of the barrel. A plunger (14), of commercial design, is received within the barrel. The plunger includes a shank (14.1), a piston (14.2) attached to the distal end of the shank, and a handle or finger grip (14.3) attached to the proximal end of the shank. The piston (14.2) is normally of rubber or other resilient material, and may have exterior rings (14.4) that engage and slideably seal against the smooth interior surface (12.8) of the barrel, all in a known fashion. The shank (14.1) commonly is generally "X"-shaped in cross-section (FIG. 6) and defines radially extending webs (14.5, 14.6, 14.7 and 14.8). The outer edges of the webs commonly are squared off to provide fairly sharp, right-angled corners; and edge (14.6) of FIG. 6 typifies an outer, squared off edge (14.9) defining, with the walls of the web, right-angled corners (15 and 15.1). Referring to FIG. 6, the shank fits loosely through the interior of the barrel and also fits loosely through the somewhat more constricted open proximal end (12.2) of the barrel defined by the annular lip (12.6), the opening (12.2) having a diameter slightly greater than the greatest distance across the webbed shank (14.1).

The locking means of the invention, designated generally as 20, is typified in FIGS. 1–7 as including cam means (22), a handle (24), and connector means (26) connecting the cam means and handle.

The cam means typified in FIGS. 2, 3 and 7, includes a generally cylindrical cam (22.1), the outer surface (22.2) of which is generally cylindrical but exhibits a more flattened surface portion (22.3) along one side, as shown best in FIG. 3, the cam thus being provided with a major diameter "x" and a minor diameter "y". The generally more flattened surface (22.3) preferably is generally cylindrical and has a radius that is approximately one-half the diameter of the interior of the barrel defined by the smooth, interior walls (12.8). The major diameter "x" is chosen so that when the cam (22.1) is positioned with its flattened surface (22.3) in contact with the smooth interior surface of the bore, the generally cylindrical surface (22.2) of the cam is supported by confronting walls (15.2 and 15.3) of the webs (14.5 and 14.8) of the plunger shank when the latter is substantially centered in the bore, all as shown in FIG. 6.

Extending axially outwardly of the cam (22.1) to the proximal end of the barrel is a generally cylindrical connector (26), the connector, in cross-section, having a peripheral shape similar to but smaller than that of the cam to provide the cam with a generally proximally-facing shoulder (22.4) (FIGS. 2 and 3). Attached to the proximal end of the connector is a handle (24) having an arm (24.1) that extends generally radially outwardly of the proximal end of the barrel so that it is manually accessible to a syringe user. The handle may be provided with a generally circular boss (24.2) that is slightly larger than the connector (26) and defines an annular shoulder (24.3) confronting the shoulder (22.4) of the cam. The confronting shoulders thus define between them a groove (24.4) typifying retaining means for preventing axial movement of the locking means (20) with respect to the barrel. The annular lip (12.6) at the open, proximal end of the barrel is received within the groove (24.4). The abutment between the cam shoulder (22.4) and the distally-facing shoulder (12.7) of the barrel lip (12.6) restrains the locking means from escaping proximally from the open end of the barrel as the plunger is withdrawn. The shoulder (24.3) of the boss (or of the handle (24.1) if the boss is eliminated) prevents the cam from sliding toward the distal end of the barrel as the plunger is pushed into the barrel.

With further reference to the embodiment of FIGS. 1–7, the handle (24) of the locking means is shown in its unlocked position in FIG. 6, the generally flattened surface (22.3) of the cam confronting the inner, smooth cylindrical surface (12.8) of the barrel and permitting the plunger to be moved inwardly and outwardly of the barrel with ease. The adjacent walls (15.2 and 15.3) of the shank webs (14.5 and 14.8) slide smoothly along the cylindrical surface (22.2) of the cam and further, as shown in FIG. 6, hold the cam to the interior wall of the barrel with the barrel lip (12.6) being retained in the groove (24.4) of the locking means to restrain the latter from axial movement with respect to the barrel. When the cam is rotated into the locked position shown in FIG. 7 (as by moving the handle in the direction shown by the arrow in FIG. 6), the cam urges the plunger shank (14.1) toward and against the opposed side of the barrel, the periphery of the cam sliding both against the inner surface of the barrel and against the adjacent surfaces (15.2 and 15.3) of the webs (14.5 and 14.8). In this position, the plunger shank edges (14.9) are urged forcefully against the confronting surface (13) of the lip, thereby restraining the plunger from further axial movement with respect to the barrel. Movement of the handle (24) from the position shown in FIG. 6 to that shown in FIG. 7 rotates the major diameter ("x") of the cam toward the barrel axis, thereby increasing the distance by which the axis of the plunger is spaced from the inner wall of the barrel adjacent the cam, and pinching or binding the shank between the barrel and the cam to lock the plunger in place.

It will further be noted that when the locking means is in the position shown in FIGS. 1 and 6, the edge (24.5) of the handle lies along and contacts the adjacent surface (15.2) of the web (14.5); similarly, when the handle has been moved to the position shown in FIG. 7, the other edge (24.6) of the handle lies along and contacts the adjacent surface (15.3) of the shank web (14.8), the shank webs in the depicted embodiments thus limiting and defining locked and unlocked positions of the cam.

The shanks of medical syringes such as that described above generally are at least slightly flexible, and the locking means of the invention can thus be inserted in such syringes simply and easily by pressing the cam portion thereof radially inwardly and distally into the generally segment-shaped space bounded by the barrel lip and confronting surfaces of the shank webs. In the embodiment shown in FIGS. 1–7, this can be accomplished in only a second or two, and the locking means becomes seated in place with an audible click.

When the locking means is in its locked position, as typified in FIG. 7, the plunger is forced to one side of the barrel and is pinched or bound between the barrel on one side and the cam on the other side, thus securely locking the plunger against axial movement with respect to the barrel. The plunger, cam or barrel, or any one or combination of these, may be provided with slots or with sharp or serrated edges if desired to more securely hold the plunger in place.

With reference to FIGS. 3, 6 and 7, it will be understood that the binding force exerted by the plunger against the barrel and cam is dictated largely by the shape and dimensions of the cam means (22). For example, the force thus exerted to lock the plunger in place can be reduced in the embodiment of FIGS. 1-7 by reducing the "x" cylindrical diameter of the cam, such reduction also reducing the amount of manual force which must be employed to rotate the cam into the position shown in FIG. 7. Further, the ease with which the plunger can be axially moved within the barrel when the locking means is in the unlocked position shown in FIG. 6 can be varied by reducing the proximity of the generally flattened surface (22.3) of the cam to the interior surface (12.8) of the barrel. It is important, of course, to insure that the locking means is axially retained in position with respect to the barrel; that is, that the barrel lip (12.6) be retained in the groove (24.4) in the embodiment of FIGS. 1-7. It is further desirable to enable the handle to be turned from the position shown in FIG. 6 to that shown in FIG. 7 with minimal manual force, and yet permit the plunger to be locked securely between the barrel and the cam when the cam is in its locked position.

It will be evident that the cam shape and size shown in FIGS. 3, 6 and 7 can be varied as desired to accomplish the desired result. In one satisfactory embodiment, a cam of the shape shown in FIG. 3 was provided with a major diameter of 0.27" inches (about 6.9 mm.) and a minor diameter of 0.2 inches (about 6.27 mm.), and was employed in the standard commercial syringe having an internal barrel diameter of approximately $\frac{5}{8}$ inches (about 15.9 mm.) and substantially as depicted in the drawing. With the locking means in its unlocked position as shown in FIG. 6, 0.87 pounds (about 395 grams) of force were required to smoothly withdraw the plunger as compared with 0.75 pounds (about 340 grams) of force that was required in the absence of the locking means. When the locking means was turned to the locked position shown in FIG. 7, 5.5 pounds (about 2.49 kilograms) were required to axially move the plunger against the locking force thus applied. Moreover, the handle arm, which was approximately $\frac{5}{8}$ths of an inch (about 15.9 mm.) long so as to protrude laterally from the open end of the barrel, could be moved readily with finger pressure from the position shown in FIG. 6 to that shown in FIG. 7.

Figure 8:
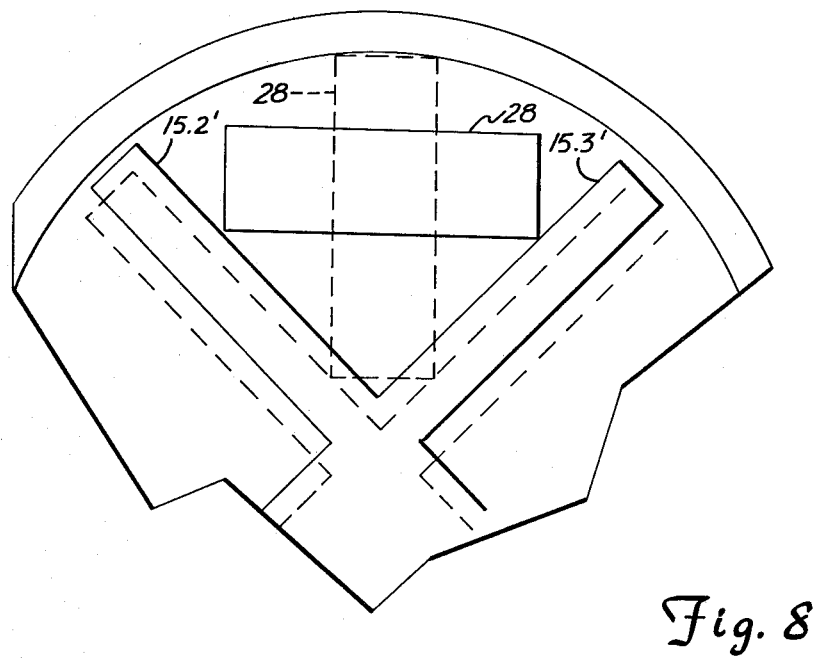
FIG. 8 is a broken-away, cross-sectional view of another embodiment of the invention.
Figure 9:
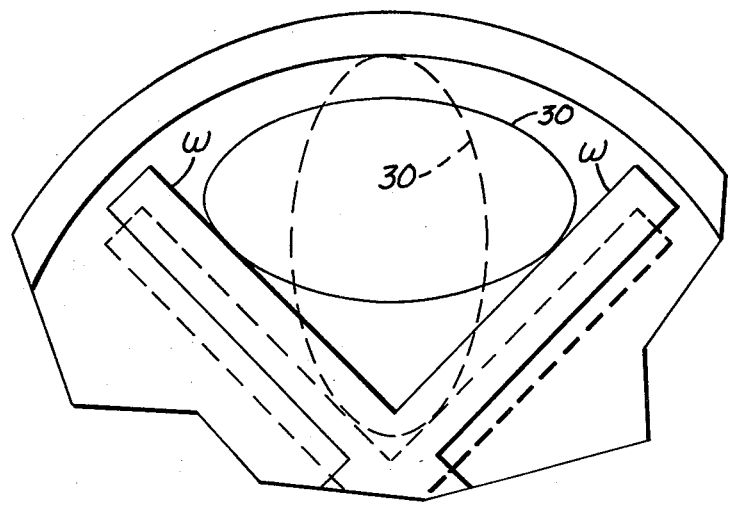
FIG. 9 is a broken-away, cross-sectional view showing a further embodiment of the invention.
Figure 10:
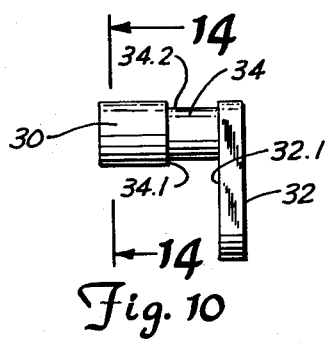
FIG. 10 is a plan view of a modified locking means of the invention.
Figure 11:
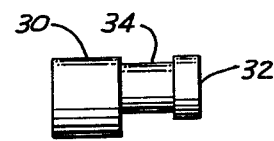
FIG. 11 is a bottom view of the locking means of FIG. 10.

Another embodiment of the locking means of the invention is shown diagrammatically in FIG. 8. In this embodiment which is identical to the embodiment shown in FIGS. 1-7 except for the shape of the cam, the cam 28 is provided with a generally rectangular cross-section having dimensions such that when the edges of the cam are in light, sliding contact with the confronting walls (15.2 and 15.3) of the shank webs when the locking means is in its unlocked position. When the cam is rotated through about 90° into the position shown in phantom lines, the cam forces the plunger shank lockingly against the opposed side of the barrel, as is also shown in phantom lines. In FIG. 9, which is the same as the embodiment of FIGS. 1-7 but for the shape of the cam, the cam 30 is provided with an elipitical shape in cross-section, and may be rotated from its unlocked position shown in solid lines to its locked position shown in phantom lines, the plunger being forced similarly from its solid line position to the position shown in phantom lines.

A preferred embodiment of the invention is shown in FIGS. 10-14 of the drawing. This embodiment is similar to the embodiment shown in FIGS. 1-7, but has a modified cam, designated (30). The cam, generally cylindrical in shape, is connected to the handle (32) by means of a generally cylindrical connector (34), the handle and connector having substantially the same shape as in the embodiment shown in FIGS. 1-7. The connector (34) and cam (30) provide a proximately facing shoulder (34.1) which cooperates with an oppositely facing shoulder (32.1) formed by the distally facing surface of the handle and the connector to form, with the surface of the connector, a groove (34.2) typifying retaining means. As in the previously described embodiments, the groove (34.2) is sized to receive the lip (12.6) of the barrel (12).

Figure 14:
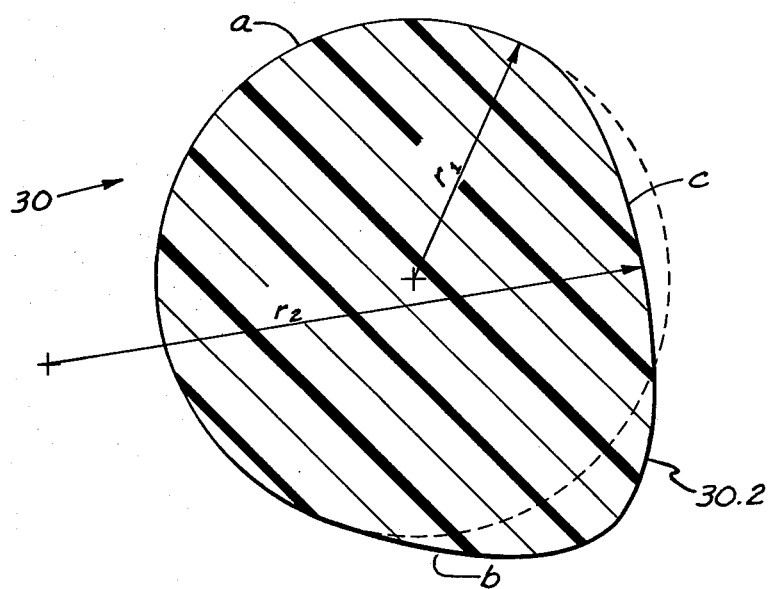
FIG. 14 is a cross-sectional view taken generally along line 14—14 of FIG. 10.

The intersection of the cam with a plane normal to the direction of travel of the plunger defines a closed curve depicted as the solid line boundary of the cross-sectional view shown in FIG. 14. One segment (a) of the closed curve is generally circular, and has a substantially constant radius ($r_1$). Another segment (c) of the closed curve also is circular in shape, but has a radius ($r_2$) substantially greater than the radius of the circular segment (a), the radius ($r_2$) being substantially the same as the radius of the internal cylindrical surface of the barrel. The circle defined by the radius ($r_1$) has been completed in dashed lines in FIG. 14 for purposes of explanation. The remaining curved segment (b) of the closed curve extends generally outwardly of and substantially beyond the locus of points generated by the radius ($r_1$) in a smooth curve, the segment (b) adjoining the generally circular segments (a) and (c). The surface (30.1) of the cam defined by the segment (b) provides a bearing surface, as described more fully below. The surfaces defined by the segments (c) and (b) merge in a smoothly rounded nose or edge designated 30.2 in FIG. 14. This projection of the camming surface beyond the circular configuration defined by the radius ($r_1$) provides the cam, in cross-section, with a slightly elongated, asymmetric shape. Referring again to FIG. 14, it will be seen that the longest chord that can be drawn across the closed curve will pass through the edge (30.2), and will be substantially greater, and preferably at least 1.2 times greater, in length than the longest chord passing through the closed curve perpendicular to the first-mentioned chord.

Figure 12:
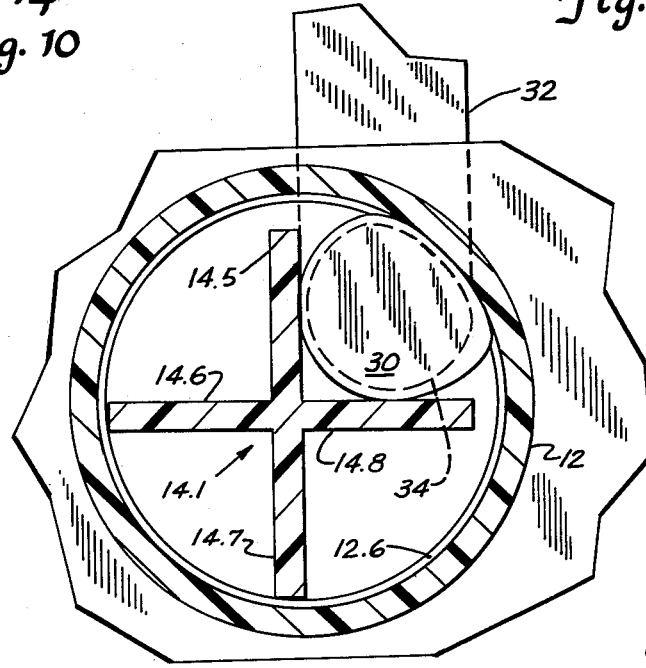
FIG. 12 is a partially broken away, cross-sectional view of a syringe including the locking means of FIGS. 10 and 11, the locking means being shown in an unlocked position; the view being taken toward the open proximal end of the barrel as in FIG. 5.

FIG. 12 shows the locking means in its unlocked position, the surface of the cam corresponding to the segment (c) lying in sliding contact with the interior surface of the barrel, the surface corresponding to the circular segment (a) lying along and in sliding contact with one of the webs (14.5) of the plunger, and the bearing surface (30.1) lying along the surface of the adjacent plunger web (14.8). In this position, the plunger is slightly off center in the barrel, but the plunger is able to move smoothly and easily inwardly and outwardly of the barrel. When it is desired to lock the plunger in place, the handle (32) of the locking means is turned downwardly (counter clockwise in the drawing) into the position shown in FIG. 13. As the cam is thus rotated, the bearing surface (30.1) bears in sliding contact against and along the confronting surface of the plunger web (14.8), and concurrently the confronting surface of the plunger web (14.5) is also urged away from the portion of the barrel between the two webs. The plunger is thus urged downwardly and to the left in FIGS. 12 and 13 and is thus clamped between the barrel wall and the cam. As the handle is initially rotated from the position shown in FIG. 12, the force of the web (14.8) against the cam tends to urge the cam to return to the position shown in FIG. 12. As the handle, and cam, continue to be rotated toward the position shown in FIG. 13, a position is reached at which the cam is urged into the position shown in FIG. 13; that is, the component of force of the plunger web (14.8) against the cam passes through the center of the cam, and the cam then snaps into the position shown in FIG. 13.

Figure 13:
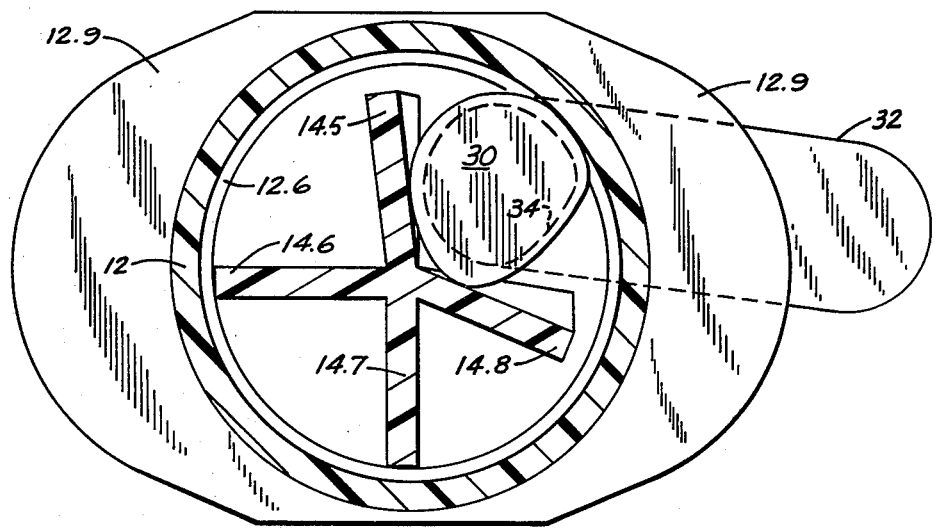
FIG. 13 is a cross-sectional view similar to FIG. 12 but showing the locking means in a locked position.

When the locking means is in its locked position, as shown in FIG. 13, the webs (14.5) and (14.8) are elastically deformed or bent somewhat as shown in FIG. 13, and, depending upon the force exerted by the cam against the plunger and barrel wall, the wall of the barrel adjacent its open end may be deformed outwardly slightly. The plunger webs and barrel, of course, substantially return to their original configurations when the locking means is returned to its unlocked position.

The locking means depicted in FIGS. 10–14 was employed in a standard commercial syringe having an internal barrel diameter of approximately ⅝ inches (about 15.9 millimeters) of the type depicted in FIG. 1. The chord of maximum length across the cam, as described above, was on the order of 0.310 inches (about 7.9 mm.) in length, and the longest chord across the cam perpendicular to the first mentioned chord was on the order of about 0.247 inches (about 6.3 mm.) in length. With the locking means in its locked position, the axial force required to cause movement of the plunger within the barrel was on the order of nine pounds (about 4.08 Kg) as compared with about 5.5 pounds (about 2.49 Kg) for the locking means depicted in FIGS. 1–7.

Various modifications may be made to the locking means of the invention, and to the syringe with which it may be used. For example, although the invention has been described above with reference to a syringe having a generally "X"-shaped plunger shank cross-sectional configuration, the invention is applicable as well to plungers having various other configurations. For example, the shank of the plunger may be substantially circular in cross-section, or may have webs defining a "Y" cross-sectional configuration. It is necessary only that the plunger and barrel define between them an open space for the reception of cam means, the latter being able to force the plunger into binding contact between the cam and the barrel when the cam is moved into its locked position.

The locking means of the invention may be manufactured of any suitable, rigid material such as metal or plastic. Preferably, the locking means, including the cam means, connector and handle is molded as an integral unit from a plastic such as polyethylene or prolypropylene or the like for purposes of high volume, low unit cost production.

Thus, there has been provided a syringe lock which is inexpensive to manufacture and simple to operate, and which in its preferred form may be employed with existing medical syringes without prior structural modification of the latter.

While a preferred embodiment of the present invention has been described, it should be understood that various changes, adaptations, and modifications may be made therein without departing from the spirit of the invention and the scope of the appended claims.

What is claimed is:

1. In a syringe having a barrel and a plunger having radially and axially extending webs and moveable axially in the barrel:
    locking means for locking the plunger to the barrel and including cam means carried by and within the barrel between the barrel and plunger, and means for moving the cam means to force the plunger into binding contact with the barrel.

2. The device of claim 1 including restraining means for restraining the cam means from axial movement with respect to the barrel.

3. The device of claim 1 wherein said means for moving the cam means comprises handle means rigidly attached to the cam and including means extending outwardly of the barrel for manual operation.

4. The device of claim 1 in which the syringe plunger includes webs extending axially along its length and radially from its axis, and in which the barrel includes a smooth, internal cylindrical wall, said wall and webs defining between them open cylindrical segments, said cam means being retained in one of said segments adjacent an open end of the barrel and having an exterior camming surface contactable with the interior surface of the barrel and with adjacent walls of the plunger webs, the cam means being rotatable between a first, unlocked position in which the plunger may readily be moved coaxially within the barrel, and a second, locked position in which the axis of the plunger is displaced in a direction normal to the axis of the barrel to bind the plunger between the barrel and cam means.

5. The device of claim 1 wherein the intersection of the cam with a plane normal to the direction of travel of the plunger defines a closed curve having a segment that is generally circular and has a substantially constant radius, and another segment that extends outwardly substantially beyond the locus of points generated by such radius.

6. The device of claim 5 in which the length of the maximum length chord across said closed curve is at least about 1.2 times the length of the longest chord across the closed curve taken perpendicular to said chord of maximum length.

7. In a syringe having a barrel with an open proximal end defined by an internally extending annular lip, and a smooth, cylindrical interior surface, and a plunger moveable axially in the barrel and having a shank comprising radially and axially extending webs spaced angularly from one another;
    locking means for locking the plunger to the barrel and including cam means carried between adjacent webs of the plunger and the interior surface of the barrel and within the barrel, the cam means having a camming surface and being rotatable from a first position in which said surface contacts walls of adjacent webs but does not substantially interfere with movement of the plunger axially within the barrel, and a second, locked position in which said camming surface contacts the interior wall of the barrel and said walls of adjacent webs, urging others of said webs into binding contact with the annular lip of the barrel.

8. The device of claim 7 including retaining means retaining the cam means in a fixed, axial relationship with respect to the barrel.

9. The device of claim 7 wherein said cam means includes a grooved, peripheral surface into which is received the annular lip of the barrel to retain the cam means in a substantially fixed, axial position with respect to the barrel.

10. The device of claim 9 wherein said cam means include manually operable handle means extending outwardly of the open end of the barrel for manual movement of the cam between its locked and unlocked positions.

11. The device of claim 7 in which the intersection of the camming surface of the cam means with a plane normal to the direction of travel of the plunger defines a closed curve having a segment that is generally circular and has a substantially constant radius, and having another segment that extends outwardly substantially beyond the locus of points generated by said radius.

12. The device of claim 7 in which the camming surface is generally rectangular in cross-section.

13. The device of claim 7 in which the camming surface is generally eliptical in cross-section.

14. In a syringe having an open proximal end, a smooth, cylindrical interior surface and an annular lip extending inwardly at its proximal end, and a plunger axially moveable within the barrel, the plunger having an elongated shank portion comprising four elongated, radially and axially extending webs, each web being oriented at right angles to adjacent webs and providing, with the interior surface of the barrel, four open, longitudinal cylindrical segments, the shank extending loosely through the open end of the barrel defined by the annular lip of the barrel;

locking means for locking the plunger axially with respect to the barrel, the locking means including a cam carried in one of said cylindrical segments, a handle extending inwardly of the open proximal end of the barrel and having an arm moveable in a plane generally normal to the axis of the barrel, and connector means rigidly joining the arm at its inner end to the cam, the locking means having a peripheral groove into which the annular lip of the barrel is received, the lip coacting with the groove to prevent axial movement of the cam with respect to the barrel, the cam having a camming surface of predetermined dimensions so that the cam, when oriented in one position with respect to the barrel, permits the plunger shank to move coaxially substantially freely within the barrel, and when oriented in a second position by rotation of the handle through an arc of approximately 90°, pressingly engages the interior surface of the barrel and the confronting surfaces of the shank webs to force other webs of the shank into binding contact with the annular lip of the barrel.

15. In a syringe having a barrel and a plunger moveable axially in the barrel:

locking means for locking the plunger to the barrel and including cam means carried by the barrel between the barrel and plunger, the cam means having a camming surface of such shape that the intersection of the cam surface with a plane normal to the direction of travel of the plunger defines a closed curve having a segment that is generally circular and has a substantially constant radius, and another segment that extends outwardly substantially beyond the locus of points generated by such radius, and means for rotating the cam means to force the plunger into binding contact between the cam means and the barrel.

16. The device of claim 15 wherein the length of the maximum length chord across the closed curve is at least about 1.2 times the length of the longest chord across the closed curve taken perpendicular to said chord of maximum length.

17. In a syringe having a barrel with a smooth, cylindrical interior surface and having an open proximal end defined by an internally extending annular lip, and a plunger moveable axially in the barrel and having a shank comprising radially and axially extending webs spaced angularly from one another;

locking means for locking the plunger to the barrel and including cam means carried between two adjacent webs of the plunger and the interior surface of the barrel, the cam means having a camming surface configured so that the intersection of the camming surface with a plane normal to the direction of travel of the plunger defines a closed curve having a first segment that is generally circular and has a substantially constant radius, a second segment formed on a larger radius approximating the radius of the cylindrical inner surface of the barrel, and a third segment extending between the first and second segments, at least a portion of the third segment extending substantially beyond the locus of points generated by the radius of the first segment, the cam means being rotatable from a first, unlocked position permitting substantially free movement of the plunger axially within the barrel, and a second, locked position in which said camming surface contacts the inner wall of the barrel and the walls of said adjacent webs to urge the plunger into binding contact between the camming surface and the annular lip of the barrel.

* * * * *